United States Patent [19]

Abel

[11] 4,198,985
[45] Apr. 22, 1980

[54] AMNIOTOMY INSTRUMENT

[76] Inventor: Philip C. Abel, 7705 Trail Ridge, Fort Worth, Tex. 76179

[21] Appl. No.: 11,318

[22] Filed: Feb. 12, 1979

[51] Int. Cl.² ............................................. A61B 17/42
[52] U.S. Cl. .................................. 128/361; 128/329 R
[58] Field of Search ................ 128/305, 314, 329, 361

[56] References Cited

U.S. PATENT DOCUMENTS

| 2,847,012 | 8/1958 | Eastman | 128/361 X |
| 3,126,890 | 3/1964 | Deming | 128/361 |
| 3,362,408 | 1/1968 | Stocki et al. | 128/314 |
| 3,587,591 | 6/1971 | Satterwhite | 128/361 |
| 3,687,139 | 8/1972 | Poirier | 128/361 |
| 3,749,099 | 7/1973 | Cotey | 128/361 |
| 3,867,947 | 2/1975 | Schack | 128/361 |

OTHER PUBLICATIONS

Stein-Jama-Feb. 9, 1935-pp. 462, 128-329.

Primary Examiner—Dalton L. Truluck
Attorney, Agent, or Firm—James E. Bradley

[57] ABSTRACT

An obstetrical instrument for rupturing an amniotic membrane for release of amniotic fluid within the membrane to facilitate the birth of a baby contained therein. The device includes a surgical glove. A hook member is bonded to the side of the long finger member, next to the index finger member and in the distal portion. The hook member has a hook on one end and is bonded at a single point at the other end to the glove. In the normal condition, the hook member is wholly contained between the two fingers. To extend the hook member for rupturing, the index finger rotates the hook member a short distance to expose the hook below the palm portions of the fingers.

7 Claims, 4 Drawing Figures

AMNIOTOMY INSTRUMENT

BACKGROUND OF THE INVENTION

1. Field of the Invention

This invention relates in general to obstetrical instruments and more particularly to an obstetrical instrument for rupturing the amniotic membrane.

2. Description of the Prior Art

The amniotic membrane is the sac enclosing the fetus. Frequently, during labor, the physician will rupture the membrane at the opening of the cervix to permit some of the fluid to be drained from the uterus so that the contracting muscles are able to push the baby through the cervical canal.

One commonly used device for performing the amniotomy is a straight rigid plastic rod about 10 inches long. The rod has a hook on one end. The operation is cumbersome and two hands are required in order to perform the rupturing. Another common method employs a clamp, which tears the membrane. Again the operation is cumbersome due to requiring both hands.

There have been several other proposals for devices for performing amniotomy. In U.S. Pat. No. 3,587,591, issued to Satterwhite, a blade is enclosed in a sheath on the top or dorsum of one of the finger members of a surgical glove. The index finger advances the blade from a retracted position to an extended position. One disadvantage of this instrument is the complexity of manufacturing it. Also, the blade is not retractable, thus could lacerate other tissue during withdrawal.

In U.S. Pat. No. 3,126,890, issued to Deming, Sr., a tooth with a sharp point is formed on the palm portion or palmer aspect of one of the finger members of a glove. The disadvantage of this device is that the operator is unable to make a preliminary examination with his finger tips. Also the tooth does not retract.

In U.S. Pat. No. 3,687,139, issued to Poirier, a rigid metal tube is inserted over the physician's finger. This tube has a sharply tipped hook that may be manipulated from a retracted position to the extended position. However, examination by the fingertips of the physician will be prevented by the tube because of the tube's thickness and rigidity.

SUMMARY OF THE INVENTION

It accordingly is a general object of this invention to provide an improved device for rupturing the amniotic membrane.

It is a further object of this invention to provide an improved device for rupturing the amniotic membrane that is operational with a single hand, that allows the physician to examine the membrane with his fingertips prior to rupturing, and is easy to operate.

It is a further object of this invention to provide an improved device for rupturing the amniotic membrane that is of simple construction, and retractable for entry and withdrawal, to avoid lacerating other tissue.

In accordance with these objects, a device is provided that includes a surgical glove. A small hook member is bonded to the side of the long finger in the distal portion and adjacent the index finger. The hook member has a hook in its forward end and is bonded to the glove at a single bonding point at its rearward end. In the natural condition, or retracted position, the hook member is completely located between the index finger and the long finger. The single point bonding allows the index finger to push the hook member into an exposed position past the palm portions of the fingers for rupturing the membrane.

DESCRIPTION OF THE PREFERRED EMBODIMENT

Figure 1:
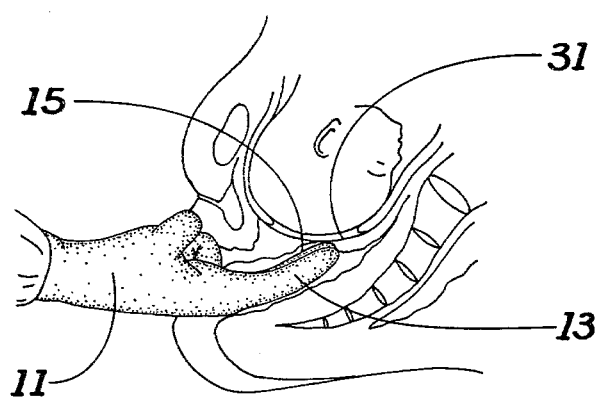
FIG. 1 is a sectional view of the female human anatomy carrying a child during pregnancy.
Figure 2:
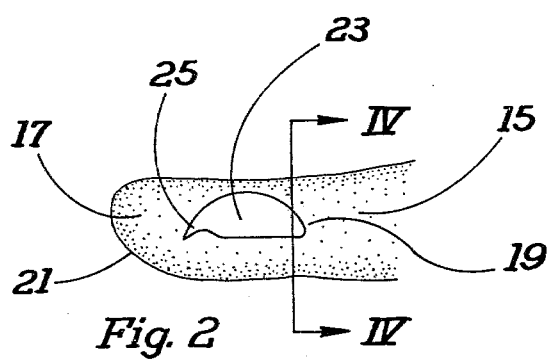
FIG. 2 is a side elevational view of a device in accordance with this invention, shown in the retracted position.
Figure 4:
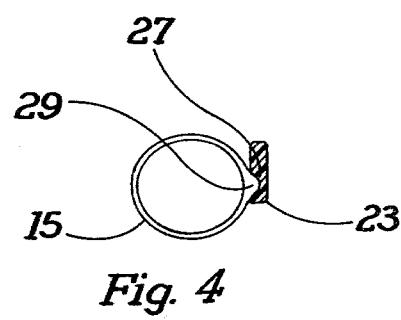
FIG. 4 is a sectional view of the device of FIG. 2, taken along the line IV—IV of FIG. 2.

Referring to FIG. 1, the gynecological instrument includes a conventional surgical glove 11. Glove 11 is of thin flexible material, impervious to moisture and capable of withstanding sterilization. Glove 11 fits tightly over the physician's or operator's hand. Referring to FIGS. 2 and 4, glove 11 has a hand portion and five finger portions, including an index finger member 13 for covering the operator's index finger, and a long finger member 15, for covering the operator's finger that is next to the index finger. Each finger member 13, 15 has a distal portion 17 extending at and from the operator's distal joint, indicated as numeral 19, to the tip of the fingers. Each finger member 13, 15 has a palm portion 21 in the distal portion 17 that is on the side of the finger members opposite the back or dorsum part of the hand.

A hook member 23 is bonded to the side of finger member 15 next to index finger member 13. Hook member 23 is a piece of thin flat hard plastic or rubber, and shaped as a segment of a circle. The upper portion of the hook member 23 is curved, while the lower portion is straight. It has a small hook 25 on its forward end that faces toward the palm portion 21. Hook 25 is located on the flat or lower edge of the hook member 23. Hook member 23 has a depression 27 on its inner side and on the end opposite the hook 25. Glove 11 has a thickened protrusion 29 located approximately at the distal joint 19 on the side of finger member 15. A strong adhesive is placed over the protrusion 29 and the depression 27, to bond the hook member 23 at this bonding point. This bonding point is the only point at which hook member 23 is secured to the glove 11. The height of hook member 23 from the flat edge to the curved edge is about one half the thickness of finger member 15. The length of hook member 23 is less than the length of the distal portion 17.

Figure 3:
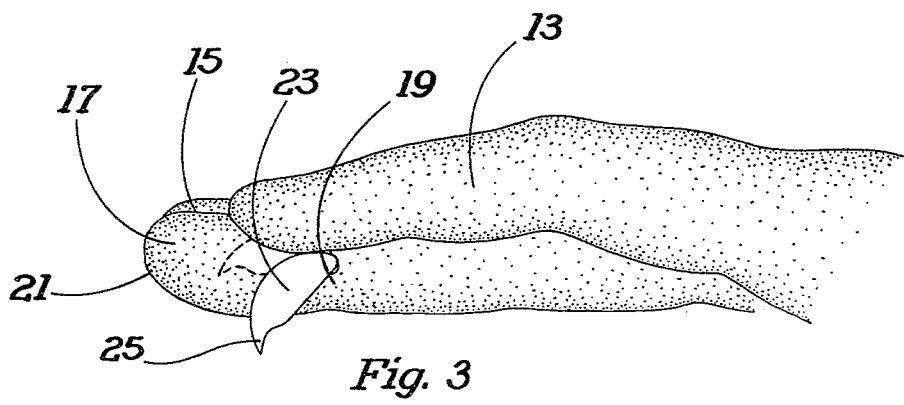
FIG. 3 is a side elevational view of the device of FIG. 2 shown in the extended position.

The operation of the instrument is illustrated in FIGS. 1 and 3. The natural or retracted position, shown in FIG. 2, is the position at which the hook member 23 has been bonded to the finger member 15. In this position, when the operator's fingers are brought together, the hook member 23 will be wholly between the index finger member 13 and the long finger member 15. No part of the hook member 23 will protrude past the palm portion 21 of the finger members 13 and 15. In this position, as shown in FIG. 1, the physician will be able to feel the amniotic membrane 31 with the palm portions of his index finger and the long finger.

When the physician has determined that a patient requires amniotomy, he first inserts his index and long fingers to examine the membrane. Once the desired point of rupturing is determined, he moves his index finger 13 back slightly and contacts the curved edge of hook member 23, pushing forwardly and toward the palm portions of the fingers a short distance as shown in FIG. 3. The flexibility of glove 11 allows the hook member to be twisted about bonding point 27, 29. This will cause the hook 25 to protrude past the palm portion 21 of the finger member, defining the extended position shown in FIG. 3. This manipulation is performed while the fingers are still inserted. The physician then inserts the sharp tip of hook 25 into the membrane 31 and draws back to rupture it. After rupturing, the physician allows the hook member 23 to rotate back into its retracted position. The twist at the bonding point, created by pushing the hook member 23, urges the hook member 23 back to retracted position when the pressure from the index finger is removed. With the two fingers together, the physician then withdraws his hand, the hook member again being wholly located between the two fingers.

If desired, while moving the hook member 23 to the extended position, the physician may slide the index finger from the curved edge of the hook member 23 to the side of it. He then holds the hook member 23 in the extended position by exerting the lateral pressure with the side of his index finger.

It should be apparent that an invention having significant improvements has been provided. The physician is able to easily and safely rupture the amniotic membrane with a single hand. The physician's fingertips are not obstructed, allowing him to make a preliminary examination. The rotation of the hook member between the retracted and extended positions is easy to perform. During entry and withdrawal, the hook is retracted to avoid lacerating other tissue. The device is of simple construction.

While the invention has been shown in only one of its forms, it should be apparent to those skilled in the art that it is not so limited but that it is susceptible to various changes and modifications without departing from the spirit thereof.

I claim:

1. An improved gynecological device for rupturing an amniotic membrane during obstetrical procedures, comprising:
    a glove having finger portions, each having a distal portion for enclosing the portion of the operator's fingers at and past the distal joint, and a palm portion on one side of the distal portion;
    a hook member bonded to a side of one of the finger members between two finger members and in the distal portion, the hook member having a hook on one end, the hook member being bonded so that in its retracted position, the hook will not protrude past the palm portion of the finger members; and
    bonding means for bonding the hook member to the finger member in a manner that allows the hook to be pushed past the palm portion of the finger member by the adjacent finger of the operator to an extended position for rupturing the membrane.

2. The device according to claim 1 wherein the bonding means comprises adhesive between the hook member and the finger member at a single bonding point and on the end of the hook member opposite the hook, the flexibility of the glove allowing the hook member to be rotated a selected distance about the bonding point to move the hook into the extended position.

3. The device according to claim 2 wherein a depression is formed in the hook member at the bonding point, and wherein the glove has a mating protrusion, to strengthen the bonding means.

4. The device according to claim 2 wherein the bonding point is located substantially at the distal joint.

5. The device according to claim 1 wherein the hook is located on the forward end of the hook member.

6. The device according to claim 1 wherein the hook member is secured to the long finger member on the side adjacent the index finger member, and the hook member is manipulated between the retracted and extended positions by the operator's index finger.

7. An improved gynecological device for rupturing an amniotic membrane during obstetrical procedures, comprising:
    a glove having finger portions, each having a distal portion for enclosing the portion of the operator's fingers at and past the distal joint, and a palm portion on one side of the distal portion;
    a hook member, having a hook on one end, and bonded at a single bonding point on its opposite end to the side of the distal portion of the long finger member that is next to the operator's index finger, the hook member being located for manipulation between a retracted position and an extended position by the operator's index finger;
    in the retracted position, the hook facing generally toward the palm portion, but being wholly located between the long finger member and the index finger;
    in the extended position, the hook member being rotated about its bonding point so that the hook protrudes past the palm portion for rupturing the membrane.

* * * * *